(12) United States Patent
Frere et al.

(10) Patent No.: US 9,107,991 B1
(45) Date of Patent: Aug. 18, 2015

(54) BREAST FEEDING FACILITATION ASSEMBLY

(71) Applicants: Tisha M. Frere, Riverview, FL (US); Kanji A. Frere, Riverview, FL (US)

(72) Inventors: Tisha M. Frere, Riverview, FL (US); Kanji A. Frere, Riverview, FL (US)

(*) Notice: Subject to any disclaimer, the term of this patent is extended or adjusted under 35 U.S.C. 154(b) by 193 days.

(21) Appl. No.: 13/792,575

(22) Filed: Mar. 11, 2013

(51) Int. Cl.
*A61M 1/06* (2006.01)
*A61M 1/00* (2006.01)

(52) U.S. Cl.
CPC .......... *A61M 1/06* (2013.01); *A61M 2001/0068* (2013.01); *A61M 2001/064* (2013.01); *A61M 2205/073* (2013.01)

(58) Field of Classification Search
CPC ............ A61M 1/06; A61M 2001/064; A61M 2001/066; A61M 2001/0068; A61M 2205/073; A61J 9/00
USPC .......... 604/73–76, 131, 65–67; 215/11.1, 396; 128/DIG. 12, DIG. 13
See application file for complete search history.

(56) References Cited

U.S. PATENT DOCUMENTS

| | | | | |
|---|---|---|---|---|
| 22,018 A * | 11/1858 | Davidson | .......................... | 604/76 |
| 22,080 A * | 11/1858 | Lewis | .............................. | 604/76 |
| 78,987 A * | 6/1868 | Elroy | ................................ | 604/76 |
| 420,195 A * | 1/1890 | Graves | ............................ | 604/76 |
| 949,414 A * | 2/1910 | Cunningham | .................. | 604/76 |
| 3,990,596 A * | 11/1976 | Hoftman | ....................... | 215/11.1 |
| 4,050,600 A * | 9/1977 | Jennings | ....................... | 215/11.1 |
| 4,934,542 A * | 6/1990 | Clark, Jr. | ....................... | 215/11.1 |
| 4,941,579 A * | 7/1990 | Lee | ................................ | 215/11.1 |
| 5,049,127 A * | 9/1991 | Yen Tseng | ....................... | 604/79 |
| 5,114,374 A * | 5/1992 | Estiva | ............................. | 446/77 |
| 5,178,291 A * | 1/1993 | Piercey | .......................... | 215/11.1 |
| 5,421,496 A * | 6/1995 | Korsinsky et al. | .......... | 224/148.2 |
| 5,480,043 A * | 1/1996 | Wingo | .......................... | 215/11.1 |
| 5,514,166 A | 5/1996 | Silver et al. | | |
| 5,571,084 A * | 11/1996 | Palmer | ............................ | 604/74 |
| 6,117,103 A * | 9/2000 | Tverskoy et al. | ............... | 604/82 |
| 6,379,327 B2 | 4/2002 | Lundy | | |
| 6,440,100 B1 * | 8/2002 | Prentiss | .......................... | 604/74 |
| 6,575,202 B2 | 6/2003 | Lafond | | |
| 6,725,492 B2 * | 4/2004 | Moore et al. | .................. | 15/104.2 |
| 6,959,827 B2 * | 11/2005 | Morano et al. | ................. | 215/396 |
| 6,968,964 B2 * | 11/2005 | Gilmore | ....................... | 215/11.1 |
| 6,988,930 B2 | 1/2006 | Gillan | | |
| 7,559,915 B2 | 7/2009 | Dao et al. | | |
| 7,607,965 B1 | 10/2009 | Frazier | | |
| 2007/0118078 A1 * | 5/2007 | McNally et al. | ............... | 604/131 |
| 2007/0161947 A1 | 7/2007 | Pfenniger et al. | | |
| 2008/0228134 A1 | 9/2008 | McKendry | | |

* cited by examiner

*Primary Examiner* — Manuel Mendez

(57) ABSTRACT

A breast feeding facilitation assembly permits discreet delivery of milk from a breast to an infant. The assembly includes a first funnel configured for coupling to a breast. A first hose has a first end coupled to the first funnel. A second end of the first hose is coupled to a pump unit wherein milk from the breast is collected by the pump unit through the first funnel. A dispersal hose has a first end coupled to the pump unit such that milk collected from the breast is dispersed into the dispersal hose. A nipple has a conduit extending through the nipple. A second end of the dispersal hose is coupled to the conduit wherein milk is pumped through the dispersal hose and the conduit by the pump unit.

13 Claims, 6 Drawing Sheets

BREAST FEEDING FACILITATION ASSEMBLY

BACKGROUND OF THE DISCLOSURE

Field of the Disclosure

The disclosure relates to breast feeding devices and more particularly pertains to a new breast feeding device for discreetly delivering milk from a breast to an infant.

SUMMARY OF THE DISCLOSURE

An embodiment of the disclosure meets the needs presented above by generally comprising a first funnel configured for coupling to a breast. A first hose has a first end coupled to the first funnel. A second end of the first hose is coupled to a pump unit wherein milk from the breast is collected by the pump unit through the first funnel. A dispersal hose has a first end coupled to the pump unit such that milk collected from the breast is dispersed into the dispersal hose. A nipple has a conduit extending through the nipple. A second end of the dispersal hose is coupled to the conduit wherein milk is pumped through the dispersal hose and the conduit by the pump unit.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
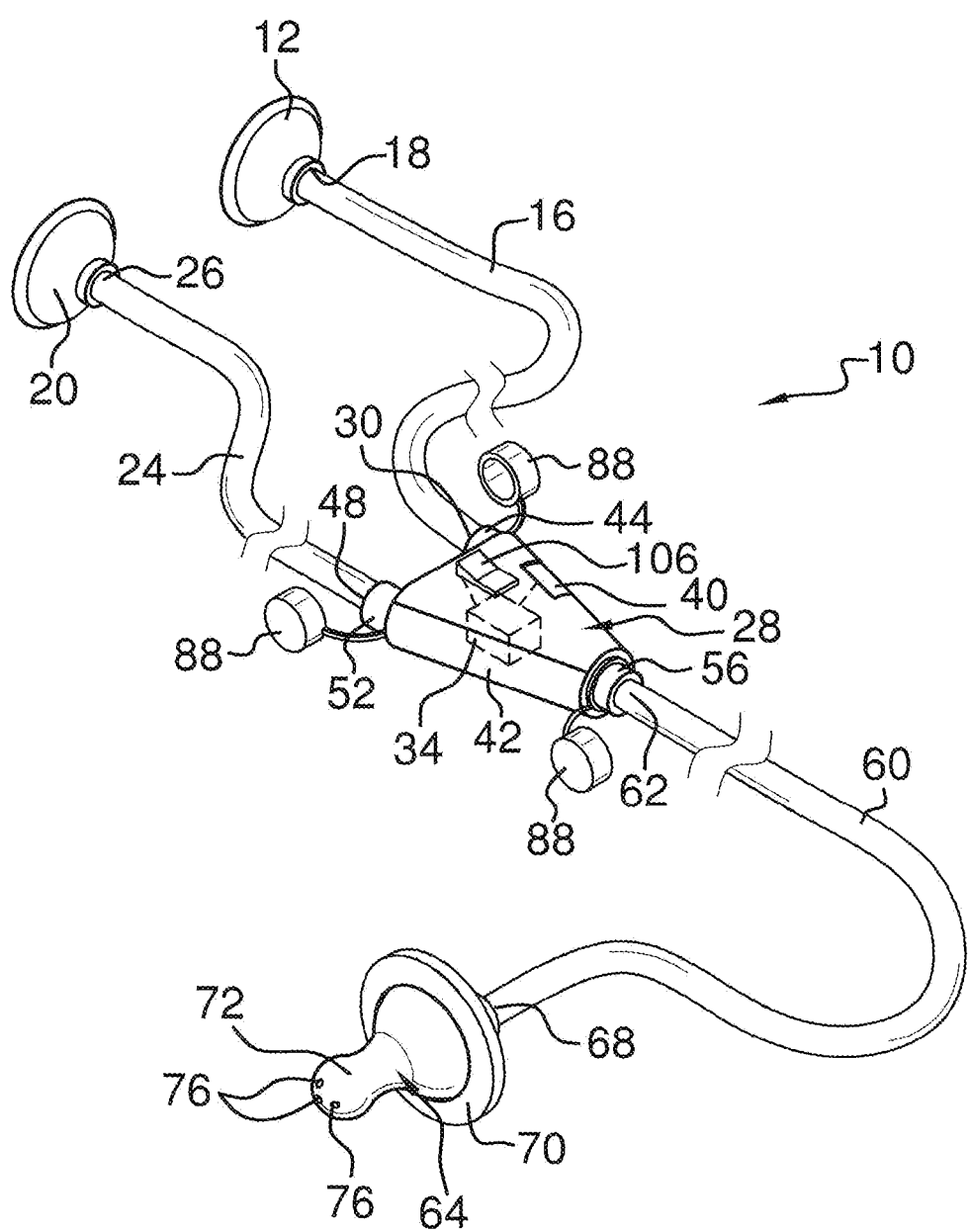
FIG. 1 is a top front side perspective view of a breast feeding facilitation assembly according to an embodiment of the disclosure.
Figure 2:
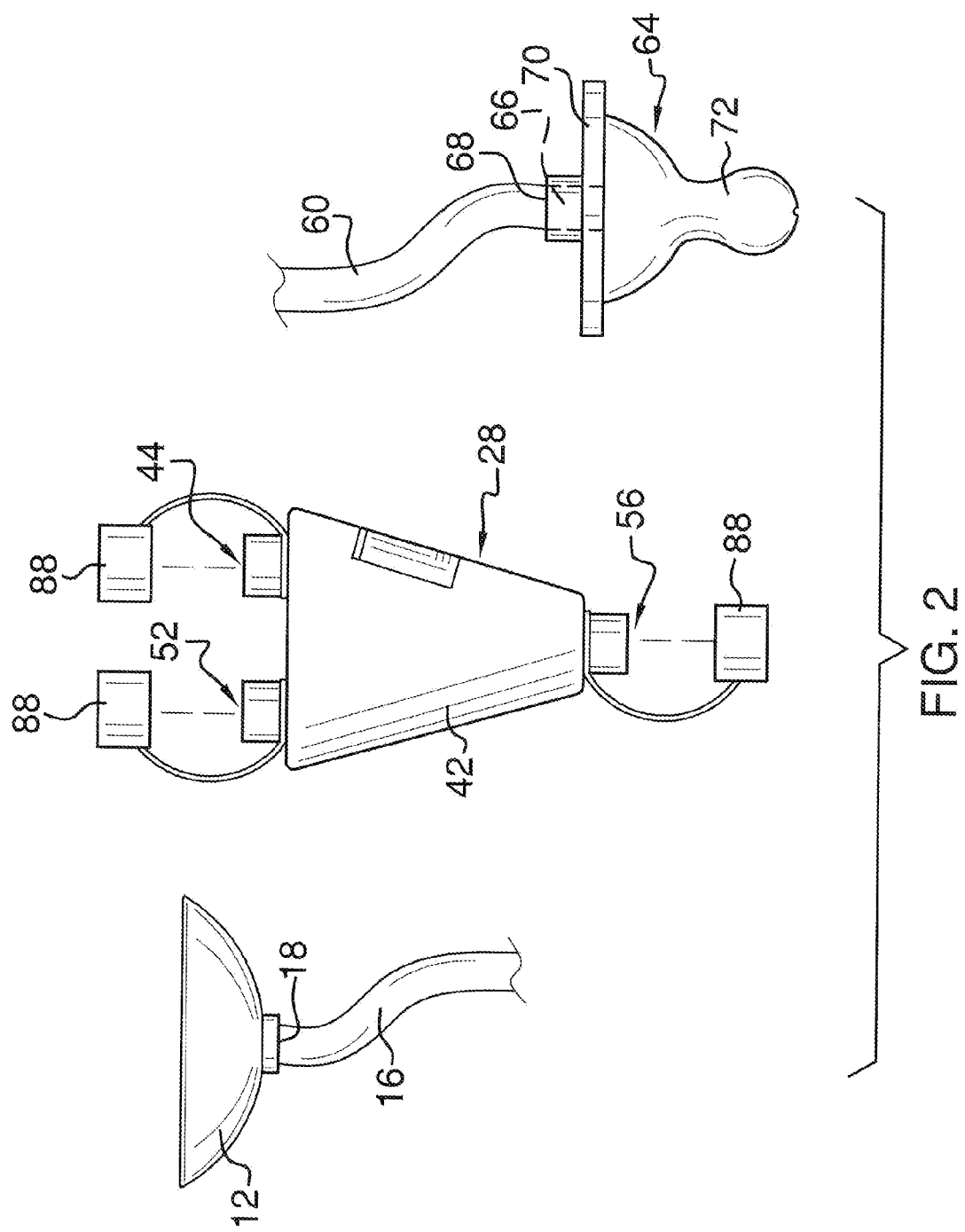
FIG. 2 is a top view of an embodiment of the disclosure.
Figure 3:
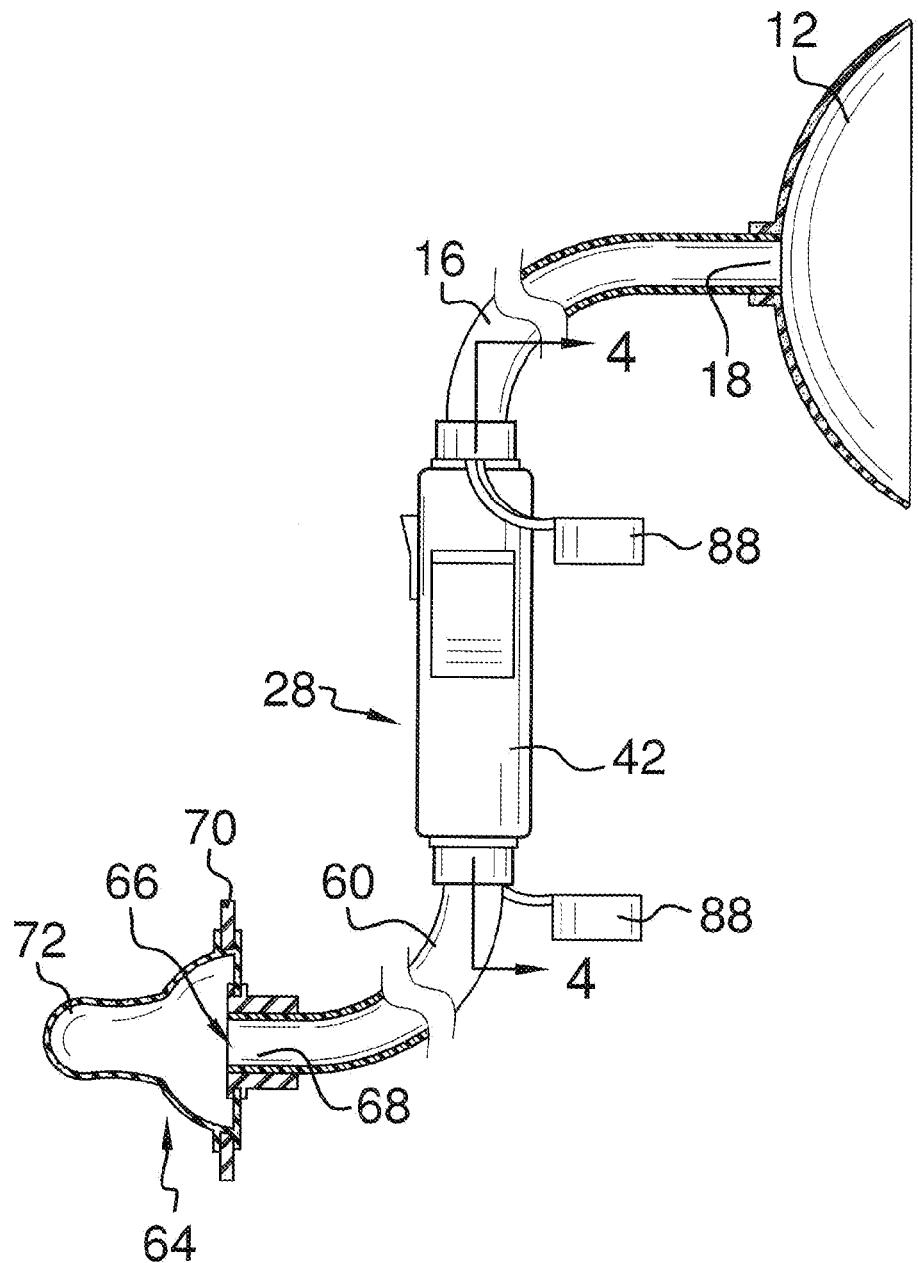
FIG. 3 is a partial cut-away side view of an embodiment of the disclosure.
Figure 4:
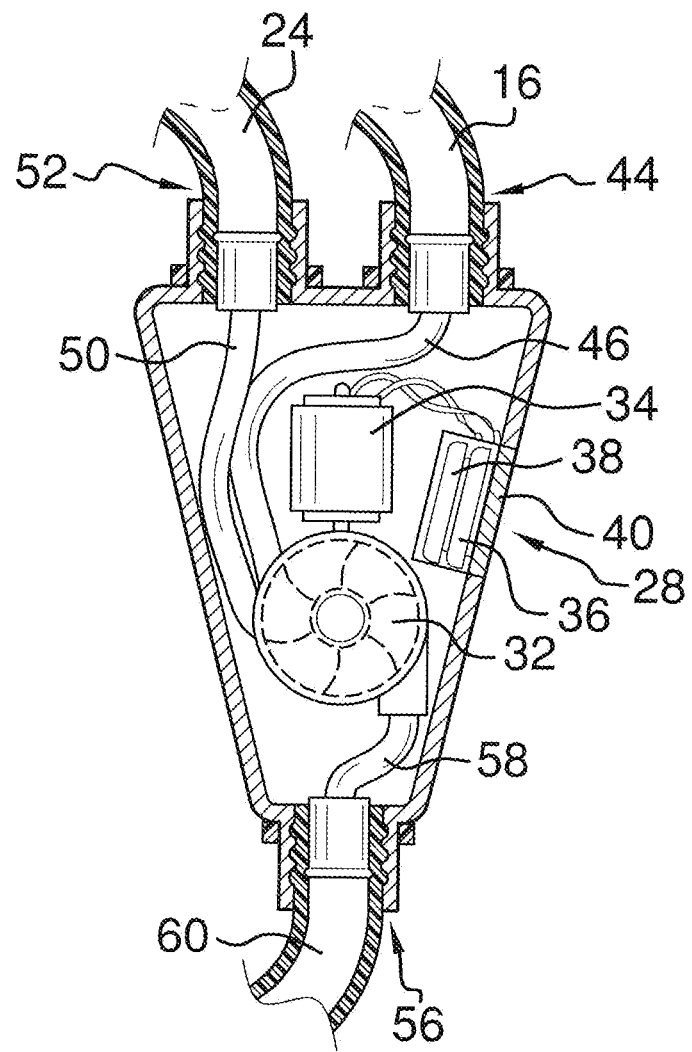
FIG. 4 is a cross-sectional view of an embodiment of the disclosure taken along line 4-4 of FIG. 3.
Figure 5:
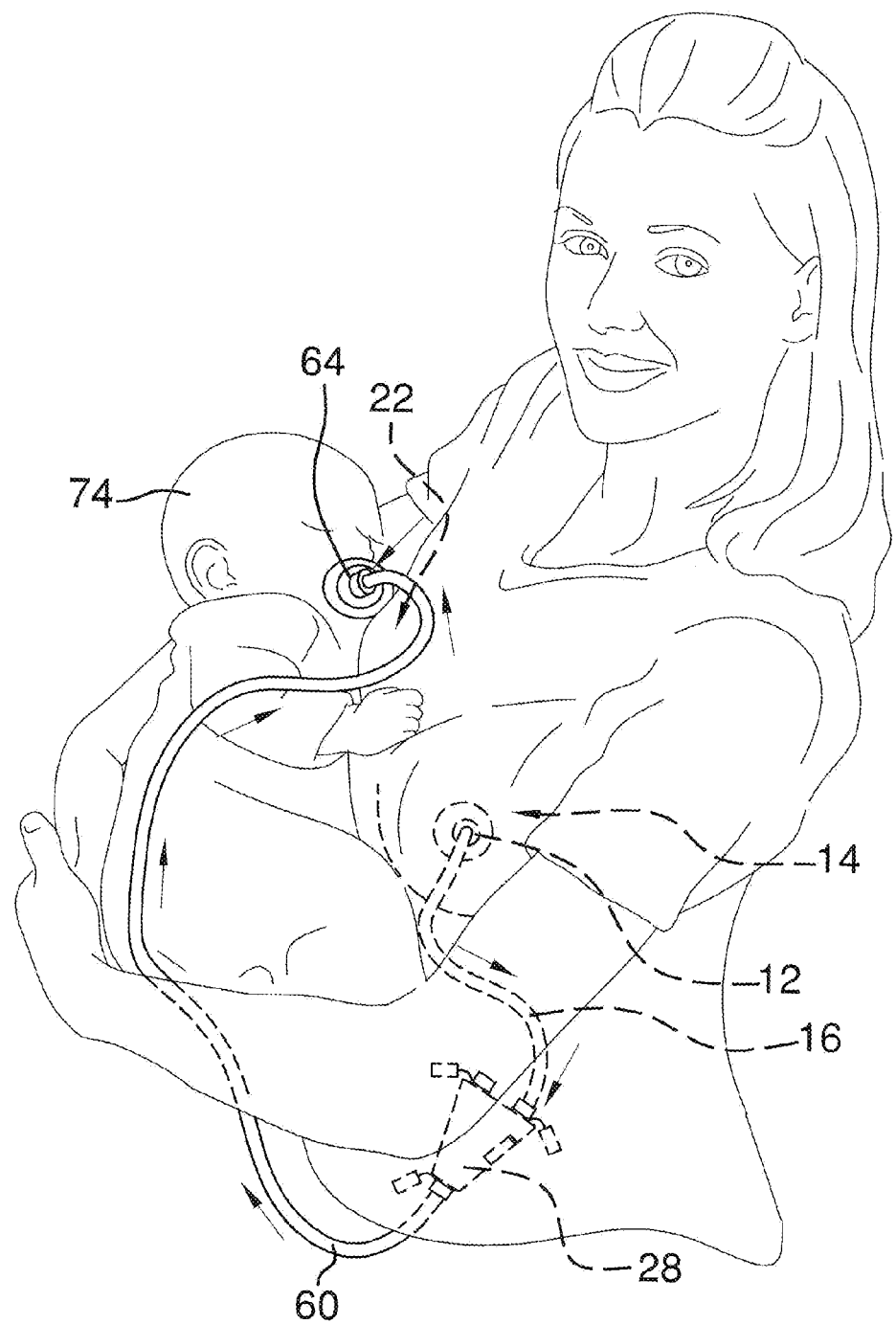
FIG. 5 is a top front side perspective view of an embodiment of the disclosure in use.
Figure 6:
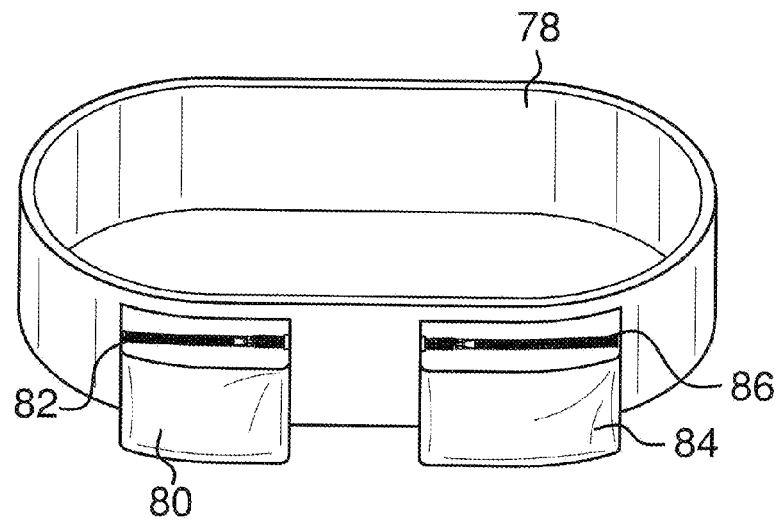
FIG. 6 is a top front view of a belt accessory of an embodiment of the disclosure.
Figure 7:
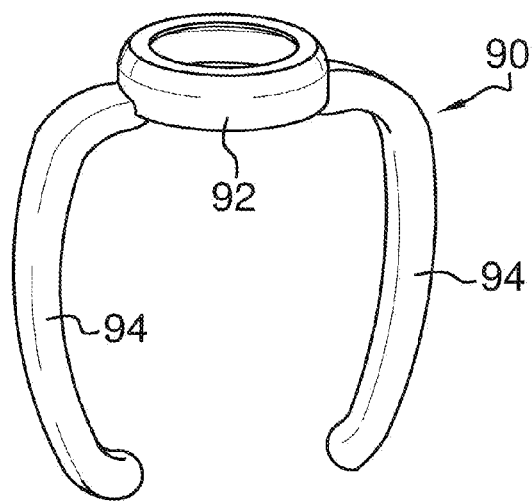
FIG. 7 is a top front side perspective view of a handle assembly of an embodiment of the disclosure.
Figure 8:
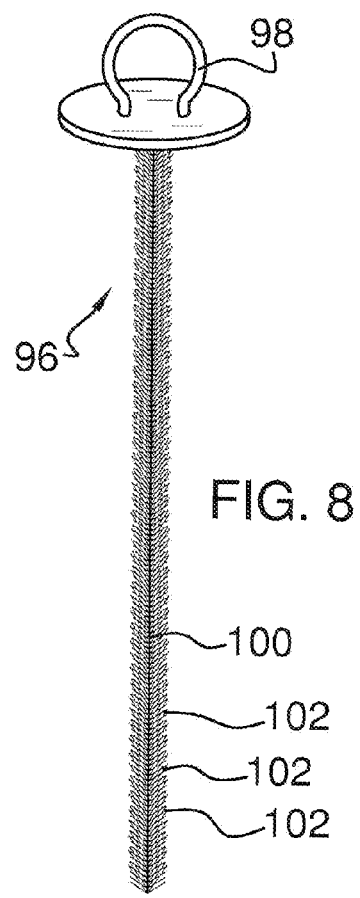
FIG. 8 is a top front side perspective view of a cleaning brush of an embodiment of the disclosure.

With reference now to the drawings, and in particular to FIGS. 1 through 8 thereof, a new breast feeding device embodying the principles and concepts of an embodiment of the disclosure and generally designated by the reference numeral 10 will be described.

As best illustrated in FIGS. 1 through 8, the breast feeding facilitation assembly 10 generally comprises a first funnel 12 configured for coupling to a first breast 14 forming a substantially air tight seal around the milk duct orifices of the first breast 14. A first hose 16 has a first end 18 coupled to the first funnel 12. A pump unit 28 is provided to pump milk from the first breast 14 as described below. A second end 30 of the first hose 16 is coupled to the pump unit 28 wherein milk from the first breast 14 is collected by the pump unit 28 through the first funnel 12. A second funnel 20 may also be configured for coupling to a second breast 22 providing a substantially air tight seal around the milk duct orifices of the second breast 22. A second hose 24 has a first end 26 coupled to the second funnel 20 and a second end 48 of the second hose 24 may be coupled to the pump unit 28 wherein milk from the second breast 22 is simultaneously collected by the pump unit 28 through the second funnel 20.

The pump unit 28 may include a housing 42 and a pump 32 coupled to and positioned in the housing 30. A motor 34 is coupled to and positioned in the housing 42. An activation switch 106 is coupled to the housing 42 and operationally coupled to the motor 34. The motor 34 is operationally coupled to the pump 32. A battery 36 is coupled to the housing 42 in a battery compartment 38 accessible through a door 40 in the housing 42. The battery 36 is electrically coupled to the motor 34. A first inlet opening 44 extends into the housing 42. The second end 30 of the first hose 16 is coupled to the first inlet opening 44. A first collection conduit 46 is coupled to and extends between the first inlet opening 44 and the pump 32 wherein suction is selectively provided through the first hose 16. A second inlet opening 52 extends into the housing 42. The second end 48 of the second hose 24 is coupled to the second inlet opening 52. A second collection conduit 50 is coupled to and extends between the second inlet opening 52 and the pump 32 to selectively provide suction through the second hose 24 when the second hose 24 is coupled to the second inlet opening 52 however the connection is such that the pump 32 provides suction through both the first collection conduit 46 and the second collection conduit 50 independently. Thus, either may be used individually to collect milk from only one of the first breast 14 and the second breast 22 if desired. An outlet opening 56 extends out of the housing 42. A dispersal conduit 58 is coupled to and extends between the pump 32 and the outlet opening 56. Caps 88 may be tethered to the pump unit 28 to selectively close the first inlet opening 44, the second inlet opening 52, and the outlet opening 56.

A dispersal hose 60 has a first end 62 coupled to the pump unit 28 wherein milk collected from the first breast 14 and the second breast 22 is dispersed into the dispersal hose 60. The first end 62 of the dispersal hose 60 is coupled to the outlet opening 56. A nipple 64 has a conduit 66 extending through the nipple 64. A second end 68 of the dispersal hose 60 is coupled to the conduit 66 wherein milk is pumped through the dispersal hose 60 and the conduit 66 extending through the nipple 64 by the pump unit 28. The nipple 64 may have a guard portion 70 coupled to and extending outwardly from the conduit 66. The nipple 64 has an insertion portion 72 coupled to and extending from the conduit 66. The insertion portion 72 is configured for being sucked upon by an infant 74 as milk is delivered through the dispersal hose 60 and conduit 66. A plurality of openings 76 may extend through the insertion portion 72 of the nipple 64 wherein milk dispersed through the dispersal hose 60 and the conduit 66 is delivered to the infant 74 through the openings 76.

A belt 78 is configured for coupling to a person. A first pouch 80 is coupled to the belt 78. The first pouch 80 has a selectively closable opening 82 into the first pouch 80. The pump unit 28 is insertable into the first pouch 80 through the opening 82 into the first pouch. 80 to store the pump unit 28 when desired. A second pouch 84 is coupled to the belt 78. The second pouch 84 has a selectively closable opening 86 into the second pouch 84. The second pouch 84 may be positioned proximate the first pouch 80 on the belt 78 such that both are accessible to one arm while holding an infant. The first hose 16, second hose 24, and the dispersal hose 60 are each insertable into the second pouch 84 through the opening 86 into the second pouch 84 for storage.

A handle assembly 90 may be provided having a ring portion 92 sized for coupling to the nipple 64. The handle assembly 90 further includes a pair of handles 94 extending from the ring portion 92. The handles 94 extending away from the nipple 64 when the ring portion 92 is coupled to the nipple 64. The handles 94 are further positioned on opposite sides of the ring portion 92 wherein the handles 94 are configured to be grasped by the infant sucking 74 while the infant 74 is sucking on the nipple 64.

A cleaning brush 96 has a gripping section 98 and a flexible shaft 100 coupled to and extending from the gripping section 98. The cleaning brush 96 includes a plurality of bristles 102 coupled to and extending from the flexible shaft 100. The bristles 102 are sized to contact a respective interior surface of the first hose 16, the second hose 24, and the dispersal hose 60 when the flexible shaft 100 is inserted into the first hose 16, the second hose 24, or the dispersal hose 60.

In use, the first funnel 12, and optionally the second funnel 20, are coupled to the first breast 14 and the second breast 22. The nipple 64 is positioned in the mouth of the infant 74 and the pump 32 of the pump unit 28 is activated. Suction is provided through the first funnel 12 and the second funnel 20 to collect milk from the first breast 14 and the second breast 22. The milk is then urged into the dispersal hose 60 and through the conduit 66 in the nipple 64 to be swallowed by the infant 74. The assembly 10 may be used discreetly as the first hose 16, second hose 24, and dispersal hose 60 permit holding the infant 74 in a natural position while milk is delivered around clothing loosely covering the first breast 14 and second breast 22.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

We claim:

1. A breast feeding facilitation assembly comprising:
a first funnel configured for coupling to a breast;
a first hose having a first end coupled to said first funnel;
a pump unit, a second end of said first hose being coupled to said pump unit wherein milk from the breast is collected by said pump unit through said first funnel;
a dispersal hose having a first end coupled to said pump unit wherein milk collected from the breast is dispersed into said dispersal hose;
a nipple having a conduit extending through said nipple, a second end of said dispersal hose being coupled to said conduit wherein milk is pumped through said dispersal hose and said conduit extending through said nipple by said pump unit such that said nipple is configured for placement directly into a mouth of an infant; and
a handle assembly having a ring portion sized for coupling to said nipple, said handle assembly further comprising a pair of handles extending from said ring portion, said handles extending away from said nipple when said ring portion is coupled to said nipple wherein said handles are configured to be grasped by the infant while sucking on said nipple.

2. The assembly of claim 1, further comprising:
a second funnel configured for coupling to a second breast; and
a second hose having a first end coupled to said second funnel, a second end of said second hose being coupled to said pump unit wherein milk from the second breast is collected by said pump unit through said second funnel and dispersed into said dispersal tube.

3. The assembly of claim 2, said pump unit comprising:
a housing;
a pump coupled to and positioned in said housing;
a first inlet opening extending into said housing, said second end of said first hose being coupled to said first inlet opening;
a second inlet opening extending into said housing, said second end of said second hose being coupled to said second inlet opening; and
an outlet opening extending out of said housing, said first end of said dispersal hose being coupled to said outlet opening.

4. The assembly of claim 3, further comprising a motor coupled to and positioned in said housing, said motor being operationally coupled to said pump.

5. The assembly of claim 4, further comprising a battery coupled to said housing, said battery being electrically coupled to said motor.

6. The assembly of claim 3, further comprising:
a first collection conduit coupled to and extending between said first inlet opening and said pump; and
a second collection conduit coupled to and extending between said second inlet opening and said pump.

7. The assembly of claim 6, further comprising a dispersal conduit coupled to and extending between said pump and said outlet opening.

8. The assembly of claim 1, further comprising said nipple having a guard portion coupled to and extending from said conduit.

9. The assembly of claim 1, further comprising said nipple having an insertion portion coupled to and extending from said conduit.

10. The assembly of claim 9, further comprising a plurality of openings extending through said insertion portion of said nipple wherein milk dispersed through said dispersal hose and said conduit through said nipple is delivered through said openings.

11. The assembly of claim 1, further comprising a cleaning brush, said cleaning brush having a gripping section and a flexible shaft coupled to and extending from said gripping section, cleaning brush including a plurality of bristles coupled to and extending from said flexible shaft, said bristles being sized to contact a respective interior surface of said first hose and said dispersal hose when said flexible shaft is inserted into said first hose and said dispersal hose.

12. A breast feeding facilitation assembly comprising:
a first funnel configured for coupling to a first breast;
a first hose having a first end coupled to said first funnel;
a second funnel configured for coupling to a second breast;
a second hose having a first end coupled to said second funnel;
a pump unit, a second end of said first hose being coupled to said pump unit wherein milk from the first breast is collected by said pump unit through said first funnel, a second end of said second hose being coupled to said pump unit wherein milk from the second breast is collected by said pump unit through said second funnel, said pump unit comprising
a housing,
a pump coupled to and positioned in said housing,
a motor coupled to and positioned in said housing, said motor being operationally coupled to said pump,
a battery coupled to said housing, said battery being electrically coupled to said motor,
a first inlet opening extending into said housing, said second end of said first hose being coupled to said first inlet opening,
a second inlet opening extending into said housing, said second end of said second hose being coupled to said second inlet opening,
a first collection conduit coupled to and extending between said first inlet opening and said pump,
a second collection conduit coupled to and extending between said second inlet opening and said pump,
an outlet opening extending out of said housing, and
a dispersal conduit coupled to and extending between said pump and said outlet opening;
a dispersal hose having a first end coupled to said pump unit wherein milk collected from the first breast and the second breast is dispersed into said dispersal hose, said first end of said dispersal hose being coupled to said outlet opening;
a nipple having a conduit extending through said nipple, a second end of said dispersal hose being coupled to said conduit wherein milk is pumped through said dispersal hose and said conduit extending through said nipple by said pump unit, said nipple having a guard portion coupled to and extending from said conduit, said nipple having an insertion portion coupled to and extending from said conduit;
a plurality of openings extending through said insertion portion of said nipple wherein milk dispersed through said dispersal hose and said conduit through said nipple is delivered through said openings; and
a handle assembly having a ring portion sized for coupling to said nipple, said handle assembly further comprising a pair of handles extending from said ring portion, said handles extending away from said nipple when said ring portion is coupled to said nipple wherein said handles are configured to be grasped by an infant sucking on said nipple.

13. The assembly of claim 1, further comprising:
a belt configured for coupling to a person;
a first pouch coupled to said belt, said first pouch having a selectively closable opening into said first pouch, said pump unit being insertable into said first pouch through said opening into said first pouch; and
a second pouch coupled to said belt, said second pouch having a selectively closable opening into said second pouch, said second pouch being positioned proximate said first pouch on said belt, said first hose and said dispersal hose being insertable into said second pouch through said opening into said second pouch.

\* \* \* \* \*